United States Patent [19]

Mizukami et al.

[11] Patent Number: 4,781,858

[45] Date of Patent: Nov. 1, 1988

[54] CYCLODEXTRIN-SILICA COMPOSITE AND A METHOD FOR THE PREPARATION THEREOF

[75] Inventors: Fujio Mizukami, Ushiku; Makoto Toba, Sakura; Shuichi Niwa; Sumi Imai, both of Yatabe, all of Japan

[73] Assignee: Director General of Agency of Industrial Science and Technology, Tokyo, Japan

[21] Appl. No.: 73,766

[22] Filed: Jul. 15, 1987

[30] Foreign Application Priority Data

Jul. 22, 1986 [JP]  Japan .................................. 61-172155

[51] Int. Cl.$^4$ ...................... A01N 25/10; A61K 9/26; B01J 13/00; B01J 13/02
[52] U.S. Cl. ................................. 252/315.2; 210/635; 424/469; 424/488; 424/493; 427/213.34; 428/402.24; 435/178; 502/404; 514/963; 514/965
[58] Field of Search .......................... 252/315.2, 315.6; 427/213.34; 428/402.24; 424/469, 488, 493; 514/963, 965

[56] References Cited

U.S. PATENT DOCUMENTS

| | | | |
|---|---|---|---|
| 3,146,252 | 8/1964 | Emblem et al. | 252/315.6 X |
| 4,169,069 | 9/1979 | Unger et al. | 428/402.24 |
| 4,432,802 | 2/1984 | Harata et al. | 424/488 X |
| 4,539,399 | 9/1985 | Armstrong | 210/502.1 X |
| 4,579,779 | 4/1986 | Ohno | 428/402.2 |
| 4,667,417 | 5/1987 | Graser et al. | 34/9 |

Primary Examiner—Richard D. Lovering
Attorney, Agent, or Firm—Wyatt, Gerber, Burke and Badie

[57] ABSTRACT

A mixture of a cyclodextrin and an alkoxy silane compound, e.g., tetraethoxy silane, is admixed with water and an acidic or alkaline catalyst, e.g., acetic acid, to effect ligand exchange and hydrolysis of the alkoxy silane followed by gelation into a gelled mass which is dried and, preferably, leached with water to remove excess of the cyclodextrin. The thus obtained gelled material is a composite having a structure in which the cyclodextrin molecules are incorporated into the matrix of amorphous silica presumably by forming Si-O-C linkages. The composite has characteristics as a combination of the properties of both of the component materials and can expand the applicability of the materials, for example, as a carrier of catalysts and immobilized enzymes, absorbent and adsorbent and so on.

13 Claims, No Drawings

CYCLODEXTRIN-SILICA COMPOSITE AND A METHOD FOR THE PREPARATION THEREOF

BACKGROUND OF THE INVENTION

The present invention relates to a novel cyclodextrin-silica composite and a method for the preparation of the same or, more particularly, to a composite, in which cyclodextrin moiety is incorporated into a matrix of amorphous silica, useful as a carrier of solid catalysts used in various chemical reactions, carrier of immobilized enzymes, microencapsulating agent of various kinds of chemical substances such as agricultural chemicals, insecticides, herbicides and photosensitive agents, filler in gel chromatography, absorbent or adsorbent, agent for material separation and purification and so on as well as a method for the preparation of such a composite.

Cyclodextrin is a recently highlighted chemical substance having a power of molecule clathration and catalytic activity and is widely used by utilizing these unique characteristics as a microencapsulating agent of various chemically unstable materials such as medicines, insecticides, herbicides and the like, solubilizing agent of some hardly soluble materials, filler in column chromatography and so on. More recently, attempts have been undertaken to modify or enhance the unique performance of cyclodextrins by introducing various functional groups into the chemical structure, by preparing a polymerized form of cyclodextrin and by preparing a composite of cyclodextrin with minerals with an object to utilize such a modified cyclodextrin as a carrier of an artificially immobilized enzyme products.

As is known, however, cyclodextrin has a chemical structure of a cyclized polysaccharide with a large number of hydroxy groups so that it is inherently not quite stable. Therefore, it is sometimes unavoidable that cyclodextrin is susceptible to structural changes by some reaction when it is used as a catalyst or encapsulating agent of artificial enzymes and photosensitive materials no longer to serve as a catalyst or encapsulating agent. In connection with the application as a filler in liquid chromatography, cyclodextrin cannot be used for the separation of materials in the form of an aqueous solution because cyclodextrin is readily dissolved in water. These disadvantages are the factors limiting the application fields of conventional cyclodextrin products.

SUMMARY OF THE INVENTION

The present invention accordingly has an object to overcome the above mentioned problems and disadvantages in the conventional cyclodextrin products and to provide a novel cyclodextrin-based product free from the above described problems and capable of exhibiting more versatile and enhanced performance. The inventors have conducted extensive investigations with the above mentioned object along the line of composite formation between cyclodextrin and an inorganic material and arrived at the establishment of the present invention described below.

Thus, the composite of the present invention is a cyclodextrin-silica composite having a structure in which the cyclodextrin moiety is incorporated into amorphous silica as the matrix.

Further, the method of the invention for the preparation of the above mentioned cyclodextrin-silica composite comprises the steps of:

(a) mixing a cyclodextrin and an alkoxysilane compound, preferably, together with a solvent to give a mixture;

(b) adding water to the mixture to cause hydrolysis of the alkoxysilane compound and gelation of the hydrolyzate to give a uniform gelled mass; and (c) drying the gelled mass.

It is sometimes advantageous, though not essential, that the thus obtained dried solid of the gelled mass is pulverized and leached with water so as to remove the excess or free cyclodextrin not incorporated into the matrix of amorphous silica.

DETAILED DESCRIPTION OF THE PREFERRED EMBODIMENTS

As is described in the above given summary of the invention, the inventive cyclodextrin-silica composite is prepared by the hydrolysis and silanol condensation of an alkoxysilane compound in the presence of a cyclodextrin to give a gelled siliceous mass, into which molecules of the cyclodextrin compound are incorporated presumably or mostly by forming Si-O-C linkages, followed by drying of the thus obtained siliceous gelled mass.

Cyclodextrin has a chemical structure of a cyclic condensate of several molecules of D-glucose and the structure of the cyclodextrin molecule is characterized by the cylindrical central hollow which serves as a receptacle to take various kinds of other molecules thereinto. The depth of the hollow is usually about 0.8 nm but the diameter of the hollow depends on the number of the D-glucose units of which the cyclodextrin molecule is composed. Conventional cyclodextrin products include $\alpha$-, $\beta$-, $\gamma$- and $\delta$-cyclodextrins composed of 6, 7, 8 and 9 molecules of D-glucose, respectively, having a diameter of the hollow ranging from about 0.5 nm to about 1.1 nm. The diameter of the hollow limits the maximum dimension of a molecule which can be taken into the hollow of the respective cyclodextrin molecules to form a clathrate. Accordingly, different cyclodextrins may differently exhibit the performance as a molecular sieve as well as activities for molecule differentiation and as a catalyst. Cyclodextrin, however, is not a quite stable compound thermally and chemically due to the presence of the large number of the hydroxy groups.

On the other hand, silica is a material having high chemical and thermal stability and amorphous silica usually has a large surface area and consequently large capacity of absorption of adsorption so that amorphous silica products are widely used as an absorbent, adsorbent and catalyst or carrier of solid catalysts. The invention cyclodextrin-silica composite is therefore characterized by the synergistic combination of the properties of the respective component materials such as the capacity of clathrate formation, molecule differentiation and molecular sieving action of the cyclodextrin and capacity for absorption and adsorption of the amorphous silica. Moreover, the composite is chemically and thermally more stable than the cyclodextrin per se to withstand severer conditions of service exhibiting higher performance. These improved characteristics of the inventive composite in comparison with cyclodextrins per se expand the application fields of the material in which high specificity and high functionality are essential as in catalysts, gel filtration materials for molecule differentiation and molecular sieving, absorbents, adsorbents, microencapsulating agents of agricultural chemicals, e.g., insecticides and herbicides, fillers in gel chromatography, carriers of artificial immobilized enzymes and many others.

The first step in the inventive method for the preparation of the above described novel cyclodextrin-silica composite is to form a mixture of a cyclodextrin and an alkoxy silane compound, preferably, together with an organic solvent. In the second step, the mixture is admixed with water to effect hydrolysis of the alkoxy silane compound into silanolic compounds which then are converted by the silanol condensation into a gelled mass of hydrated silica into which molecules of the cyclodextrin are incorporated. The solid-liquid mixture of the cyclodextrin and alkoxy silane is uniformized by the addition of water to dissolve the cyclodextrin so that the above mentioned process proceeds in a homogeneous mixture to give a uniform gelled mass. In the third step, the thus formed uniform gelled mass is dried to give the desired cyclodextrin-silica composite, in which the molecules of the cyclodextrin are presumably and mostly bonded to the structure of silica by forming Si-O-C linkages. It is sometimes advantageous that the dried mass of siliceous gel is finely pulverized and leached by using water to remove free cyclodextrin not incorporated into the matrix of amorphous silica followed by drying.

The type of the cyclodextrin used in the above described inventive method is not particularly limitative including various kinds of cyclized saccharides such as the so-called $\alpha$-, $\beta$-, $\gamma$- and $\delta$-cyclodextrins composed of 6, 7, 8 and 9 D-glucose molecules, respectively. Derivatives thereof can also be used provided that the basic structure of cyclodextrin is retained.

The alkoxy silane compound as the silica source in the inventive method is also not particularly limitative in respect of the number of the carbon atoms in the alkoxy groups. It is, however, preferable that the alkoxy groups in the alkoxy silane compound should be lower alkoxy groups including methoxy, ethoxy, propoxy and butoxy groups. Suitable alkoxy silane compounds include tetraalkoxysilanes such as tetramethoxy, tetraethoxy, tetrapropoxy and tetrabutoxy silanes, of which tetraethoxy silane is preferred. If desired, the alkoxy silane compound can be admixed with a minor amount of a silicon tetrahalide such as silicone tetrafluoride, silicon tetrachloride and silicon tetrabromide.

As is mentioned above, the mixture of the cyclodextrin and alkoxy silane compound should preferably be diluted with an organic solvent to adequately control the velocity of hydrolysis and gel formation. Suitable organic solvents include mono- and dihydric alcohols, ketones, ketoalcohols, ethers, aminoalcohols, acid amides and the like. These organic solvents can be used either singly or as a combination of two kinds or more according to need.

Further, the reactions of ligand exchange between the alkoxy groups and the cyclodextrin molecules as well as the hydrolysis and silanol condensation of the silane compound can be accelerated by adding an acid or base to the mixture as a catalyst. Though not particularly limitative, the acid or base should preferably be a lower carboxylic acid, e.g., acetic acid, or lower amine in view of the vaporizability, especially, when any trace amount of the acid or base remaining in the composite is undesirable. When a small portion of the alkoxy silane compound is replaced with a silicon tetrahalide, e.g., silicon tetrachloride, as is mentioned above, hydrolysis of the silicon tetrachloride produces hydrogen chloride which may serve as the catalyst to promote the reactions of ligand exchange as well as hydrolysis and gelation of the alkoxy silane compound. The reaction of hydrolysis of the alkoxy silane compound followed by the gelation of the mixture should be performed at a temperature in the range from 20° to 150° C. or, preferably, from 40° to 80° C., though not particularly limitative, from the standpoint of obtaining a moderate reaction velocity and in consideration of the thermal stability of the cyclodextrin.

The amount of the alkoxy silane compound in the reaction mixture should be at least equimolar to or, preferably, several times by moles of the cyclodextrin. In particular, the molar ratio of cyclodextrin to alkoxy silane should be in the range from $10^{-6}$ to 1 or, preferably, from $10^{-4}$ to 1. When the amount of the alkoxy silane compound is too small, a substantial amount of the cyclodextrin may be left as unincorporated into the matrix of the gelled silica merely to be washed away in the leaching procedure with water although the composite may contain only an insufficient amount of the cyclodextrin moiety incorporated into the matrix of amorphous silica when the amount of the alkoxy silane compound is too large relative to the cyclodextrin in the reaction mixture. The amount of water added to the mixture of the alkoxy silane compound and cyclodextrin to effect hydrolysis of the silane compound should be in the range from 1 to 100 moles or, preferably, from 2 to 30 moles per mole of the alkoxy silane compound though not particularly limitative thereto. When the amount of added water is too small, the alkoxy groups in the alkoxy silane compound are partly left unhydrolyzed while an excessively large amount of water may be detrimental against formation of strong bonding between the cyclodextrin molecules and the gelled silica matrix in the composite. The temperature at which the gelled mass is dried or dehydrated into a dry solid should not exceed the decomposition temperature of the cyclodextrin. For example, the gelled mass can be dried in a rotary evaporator under reduced pressure at a temperature of 50° to 100° C. into a dry form of the gel.

The cyclodextrin-silica composite of the invention prepared in the above described manner has a structure in which molecules of the cyclodextrin are incorporated into the matrix of amorphous silica by forming chemical linkages of Si-O-C. This conclusion is supported by the facts that the same procedure as above excepting omission of the alkoxy silane compound leads merely to almost complete recovery of the cyclodextrin, that the X-ray diffraction diagram of the composite shows no clearly identified diffraction peaks, that the thermal analysis of the composite shows a heat evolution accompanied by a weight loss in the range from 300° to 450° C. and that the infrared absorption spectrum of the composite has very good similarity to that of the cyclodextrin per se.

Thus, it would be a fair assumption that the cyclodextrin-silica composite of the invention may have high and special performance including the capabilities for molecule clathration, molecular sieving, molecular catalysis and molecule differentiation of cyclodextrin combined with the capabilities for absorption and adsorption, material separation and catalysis of silica gel and also a synergistic effect of the two components can be expected. Further characteristically, the cyclodextrin-silica composite of the invention is thermally and chemically more stable than the cyclodextrin per se and insoluble in water. By virtue of these advantageous characteristics, the cyclodextrin-silica composite of the invention is useful in many applications, for example, as a catalyst or carrier of an artificial immobilized enzyme having high selectivity and capable of being easily separated from the reaction product and suitable for continuous reactions, adsorbent for material separation having a capacity of molecule differentiation, long-life encapsulating agent of medicines and fluorescent substances, high-performance filler in chromatography and agent for resolution of geometrical and optical isomers.

In the following, the cyclodextrin-silica composite and the method for the preparation thereof according to the invention are described in more detail by way of examples.

EXAMPLE 1

Into a beaker of 200 ml capacity were taken 51.1 g of ethyl alcohol, 10.0 g of α-cyclodextrin and 40.6 g of tetraethoxy silane to form a mixture under agitation. The mixture in the beaker was then admixed with 5.3 g of acetic acid and agitated for 3 hours at a temperature of 60° to 80° C. Thereafter, the mixture was admixed with 75 g of water and further agitated at 70° to 80° C. so that mixture was converted into a uniform solution and the viscosity of the solution was gradually increased finally resulting in gelation of the solution into a jelly-like uniform mass. The gelled mass was broken into lumps which were subjected to drying in an eggplant-type flask of 200 ml capacity on a rotary evaporator at 80° C. under reduced pressure for 24 hours. The dried gel was finely pulverized and put into 400 ml of water in which the powder was agitated and then recovered by filtration followed by washing successively with ethyl alcohol and acetone and drying on a rotary evaporator. The yield of the thus obtained white powdery composite was about 17 g.

The powdery gel had an amorphous structure as indicated by the absence of any diffraction peaks in the powder X-ray diffractometric diagram ascribable to a crystalline structure. The infrared absorption spectrum of this powdery material had very good similarity to that of α-cyclodextrin. Further, the thermal analysis undertaken of this powdery gel indicated a great weight loss at a temperature in the range from 300° to 420° C. accompanied by evolution of heat.

EXAMPLE 2

Into a beaker of 300 ml capacity were taken 50.8 g of ethyl alcohol, 11.4 g of β-cyclodextrin, 6.0 g of acetic acid and 131.7 g of tetraethoxy silane and the mixture was agitated for 2 hours at 60° to 70° C. Thereafter, the mixture was admixed with 123.5 g of water so that the mixture was converted into a uniform solution which was further agitated at 65° to 75° C. The viscosity of the solution was gradually increased and the solution was finally gelled and solidified into a jelly-like uniform mass. The gelled mass was dried and pulverized in the same manner as in Example 1 and a 20 g portion of the powder was agitated for 2 hours in 500 ml of water followed by filtration, washing with ethyl alcohol and acetone and drying. The amount of the thus obtained white powdery material was about 17.5 g.

The powdery gel had an amorphous structure as indicated by the absence of any diffraction peaks in the powder X-ray diffractometric diagram ascribable to a crystalline structure. The infrared absorption spectrum of this powdery material had very good similarity to that of β-cyclodextrin including all of the characteristic absorption bands of β-cyclodextrin. Further, the thermal analysis undertaken of this powdery gel indicated a great weight loss at a temperature in the range from 300° to 400° C. accompanied by evolution of heat showing a peak at 351° C. in the DTA diagram.

EXAMPLE 3

Into a beaker of 200 ml capacity were taken 40.0 g of ethyl alcohol, 4.3 g of γ-cyclodextrin, 4.9 g of acetic acid and 50.4 g of tetraethoxy silane and the mixture was agitated for 3 hours at 70° C. Thereafter, the mixture was admixed with 60.7 g of water so that the mixture was converted into a uniform solution which was further agitated at the same temperature. The viscosity of the solution was gradually increased and the solution was finally gelled and solidified into a jelly-like uniform mass. The gelled mass was dried in the same manner as in Example 1. The yield of the dried gel was 20.5 g. The dry gel was pulverized and the powder was agitated in 400 ml of water followed by filtration, washing with ethyl alcohol and acetone and drying at 100° C. The yield of the thus obtained white powdery material was about 19.0 g.

The powdery gel had an amorphous structure as indicated by the absence of any diffraction peaks in the powder X-ray diffractometric diagram ascribable to a crystalline structure. The infrared absorption spectrum of this powdery material had very good similarity to that of γ-cyclodextrin. Further, the thermal analysis undertaken of this powdery gel indicated a great weight loss at a temperature in the range from 280° to 450° C. accompanied by evolution of heat showing a peak at 360° C. in the DTA diagram.

What is claimed is:

1. A cyclodextrin-silica composite having a structure composed of amorphous silica and a cyclodextrin incorporated into the matrix of the amorphous silica, being further characterized by the fact that the cyclodextrin is principally bonded to the silica by Si-O-C linkages.

2. A method for the preparation of a cyclodextrin-silica composite having a structure composed of amorphous silica and a cyclodextrin incorporated into the matrix of the amorphous silica being further characterized by the fact that the cyclodextrin is principally bonded to the silica by Si-O-C bonds which comprises the steps of:
   (a) mixing a cyclodextrin and an alkoxy silane compound to give a mixture;
   (b) adding water to the mixture to cause hydrolysis of the alkoxy silane compound and gelation of the hydrolyzate to give a gelled mass; and
   (c) drying the gelled mass.

3. The method as claimed in claim 2 wherein the cyclodextrin is selected from the group consisting of α-, β-, γ- and δ-cyclodextrins.

4. The method as claimed in claim 2 wherein the alkoxy silane compound is selected from the group consisting of tetramethoxy silane, tetraethoxy silane, tetrapropoxy silane and tetrabutoxy silane.

5. The method as claimed in claim 2 wherein the amount of the alkoxy silane compound mixed with the cyclodextrin in step (a) is at least equimolar to the cyclodextrin.

6. The method as claimed in claim 2 wherein the amount of water added to the mixture in step (b) is in the range from 1 to 100 moles per mole of the alkoxy silane compound.

7. The method as claimed in claim 2 wherein the mixture of the cyclodextrin and alkoxy silane compound is diluted by adding an organic solvent.

8. The method as claimed in claim 7 wherein the organic solvent is selected from the group consisting of methyl alcohol, ethyl alcohol, propyl alcohol and butyl alcohol.

9. The method as claimed in claim 2 wherein the mixture in step (b) is admixed with an acid or a base.

10. The method as claimed in claim 9 wherein the acid is selected from the group consisting of acetic acid, propionic acid, butyric acid and hydrogen chloride.

11. The method as claimed in claim 2 wherein the temperature of the mixture in step (b) is in the range from 40° to 80° C.

12. The method as claimed in claim 2 which further comprises the step of: (d) leaching the gelled mass after drying in step (c) with water to remove an excess amount of the cyclodextrin not incorporated into the matrix of the amorphous silica.

13. The method as claimed in claim 2 wherein the amount of the cyclodextrin mixed with the alkoxy silane compound in step (a) is in the range from $10^{-6}$ to 1 mole per mole of the alkoxy silane compound.

* * * * *